US006392410B2

(12) United States Patent
Luong et al.

(10) Patent No.: US 6,392,410 B2
(45) Date of Patent: May 21, 2002

(54) NUCLEAR MAGNETIC RESONANCE APPARATUS AND METHOD FOR GENERATING AN AXISYMMETRIC MAGNETIC FIELD HAVING STRAIGHT CONTOUR LINES IN THE RESONANCE REGION

(75) Inventors: Bruno Luong, Stafford; Krishnamurthy Ganesan; Martin E. Poitzsch, both of Sugar Land, all of TX (US)

(73) Assignee: Schlumberger Technology Corporation, Houston, TX (US)

( * ) Notice: Subject to any disclaimer, the term of this patent is extended or adjusted under 35 U.S.C. 154(b) by 0 days.

(21) Appl. No.: 09/864,437

(22) Filed: May 24, 2001

Related U.S. Application Data

(62) Division of application No. 09/033,965, filed on Mar. 3, 1998.

(51) Int. Cl.[7] .................................................. G01V 3/00
(52) U.S. Cl. ........................................................ 324/303
(58) Field of Search ................................. 324/303, 300, 324/318, 322, 321, 319, 320

(56) References Cited

U.S. PATENT DOCUMENTS 4,350,955 A * 9/1982 Jackson et al. ............. 324/303
5,705,927 A * 1/1998 Sezginer et al. ............ 324/303
6,114,851 A * 9/2000 Kruspe et al. .............. 324/303

* cited by examiner

Primary Examiner—Louis Arana
(74) Attorney, Agent, or Firm—John J. Ryberg; Brigitte L. Jeffery

(57) ABSTRACT

The present invention is directed to a nuclear magnetic resonance apparatus and method for generating an axisymmetric magnetic field having long, straight contour lines in the resonance region. A magnetically permeable member is used to shape the static magnetic field generated by an array of permanent magnets. The magnetically permeable member minimizes variations of the static magnetic field in the formation due to vertical motion of the apparatus while obtaining a nuclear magnetic resonance measurement. Further, the magnetically permeable member may minimize variations of the static magnetic field in the formation due to lateral motion of the apparatus while obtaining a nuclear magnetic resonance measurement.

32 Claims, 12 Drawing Sheets

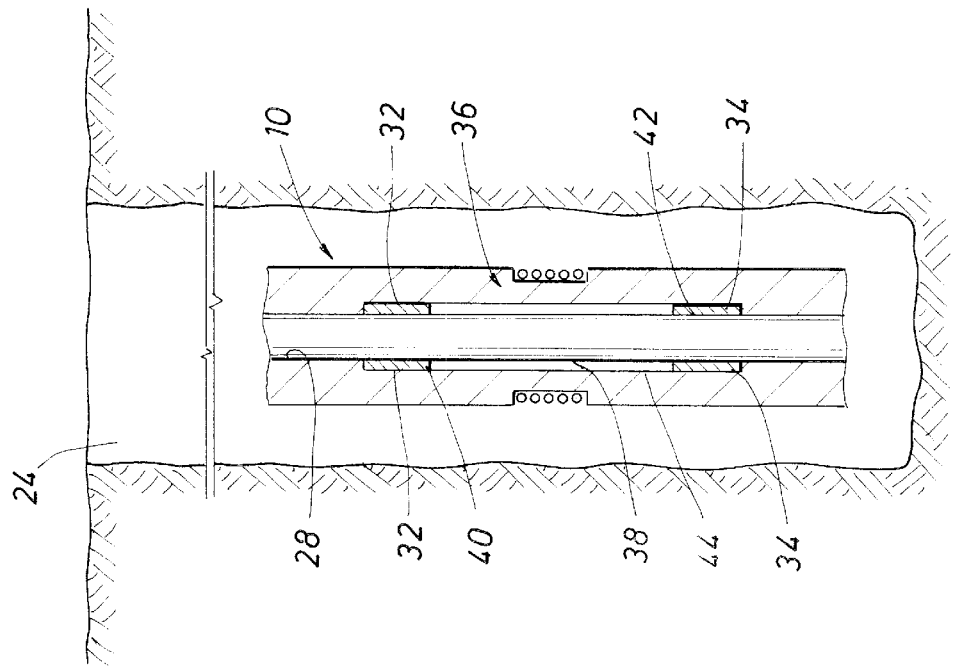
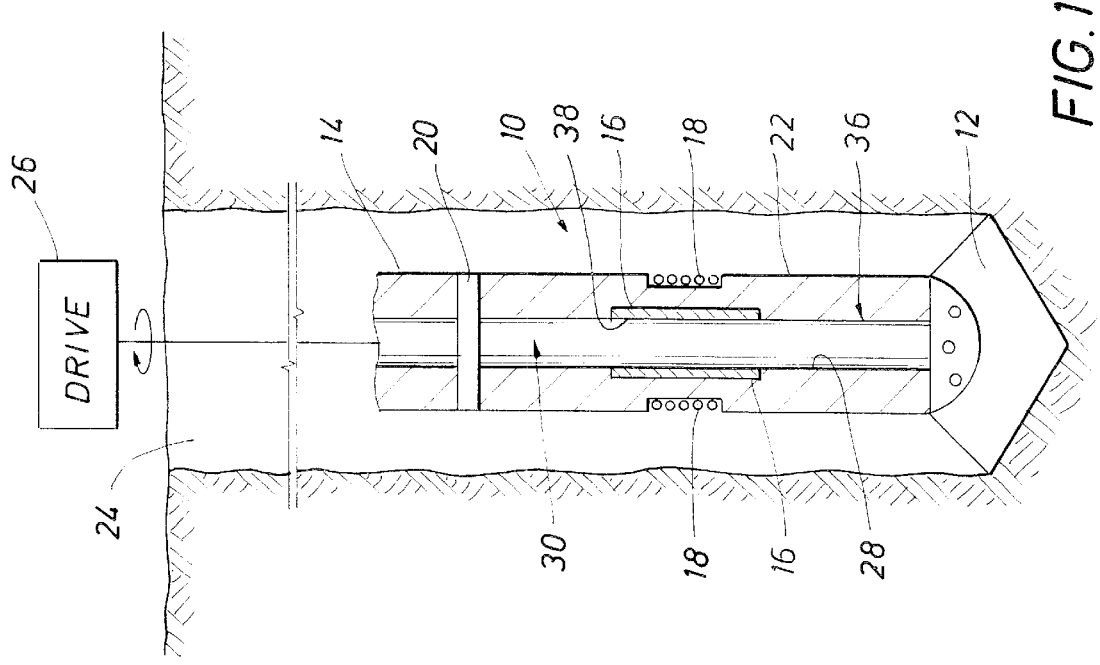

NUCLEAR MAGNETIC RESONANCE APPARATUS AND METHOD FOR GENERATING AN AXISYMMETRIC MAGNETIC FIELD HAVING STRAIGHT CONTOUR LINES IN THE RESONANCE REGION

This is a division of U.S. patent application Ser. No. 09/033,965 filed Mar. 3, 1998.

BACKGROUND OF THE INVENTION

The present invention relates generally to an apparatus and method for measuring nuclear magnetic resonance properties of an earth formation traversed by a borehole, and more particularly, to an apparatus and method for generating a substantially axisymmetric static magnetic field having long, straight contour lines in the resonance region.

It is well recognized that particles of an earth formation having non-zero nuclear spin magnetic moment, for example protons, have a tendency to align with a static magnetic field imposed on the formation. Such a magnetic field may be naturally generated, as is the case for the earth's magnetic field, $B_E$. After an RF pulse applies a second oscillating magnetic field $B_1$ transverse to $B_E$, the protons will tend to precess about the $B_E$ vector with a characteristic resonance or Larmor frequency $\omega_L$ which depends on the strength of the static magnetic field and the gyromagnetic ratio of the particle. Hydrogen nuclei (protons) precessing about a magnetic field $B_E$ of 0.5 gauss, for example, have a characteristic frequency of approximately 2 kHz. If a population of hydrogen nuclei were made to precess in phase, the combined magnetic fields of the protons can generate a detectable oscillating voltage, known to those skilled in the art as a free induction decay or a spin echo, in a receiver coil. Hydrogen nuclei of water and hydrocarbons occurring in rock pores produce nuclear magnetic resonance (NMR) signals distinct from signals arising from other solids.

U.S. Pat. No. 4,717,878 issued to Taicher et al. and U.S. Pat. No. 5,055,787 issued to Kleinberg et al., describe NMR tools which employ permanent magnets to polarize hydrogen nuclei and generate a static magnetic field, $B_0$, and RF antennas to excite and detect nuclear magnetic resonance to determine porosity, free fluid ratio, and permeability of a formation. The atomic nuclei align with the applied field, $B_0$, with a time constant of $T_1$. After a period of polarization, the angle between the nuclear magnetization and the applied field can be changed by applying an RF field, $B_1$, perpendicular to the static field $B_0$, at the Larmor frequency $f_L = \gamma B_0/2\pi$, where y is the gyromagnetic ratio of the proton and $B_0$ designates the static magnetic field strength. After termination of the RF pulse, the protons begin to precess in the plane perpendicular to $B_0$. A sequence of refocusing RF pulses generates a sequence of spin-echoes which produce a detectable NMR signal in the antenna.

U.S. Pat. No. 5,557,201 describes a pulsed nuclear magnetism tool for formation evaluation while drilling. The tool includes a drill bit, drill string, and a pulsed nuclear magnetic resonance device housed within a drill collar made of nonmagnetic alloy. The tool includes a channel, within the drill string and pulsed NMR device, through which drilling mud is pumped into the borehole. The pulsed NMR device comprises two tubular magnets, which are mounted with like poles facing each other, surrounding the channel, and an antenna coil mounted in an exterior surface of the drill string between the magnets. This tool is designed to resonate nuclei at a measurement region known to those skilled in the art as the saddle point.

Great Britain Pat. App. No. 2 310 500, published on Aug. 27, 1997, describes a measurement-while-drilling tool which includes a sensing apparatus for making nuclear magnetic resonance measurements of the earth formation. The NMR sensing apparatus is mounted in an annular recess formed into the exterior surface of the drill collar. In one embodiment, a flux closure is inserted into the recess. A magnet is disposed on the outer radial surface of the flux closure. The magnet is constructed from a plurality of radial segments which are magnetized radially outward from the longitudinal axis of the tool. The flux closure is required to provide suitable directional orientation of the magnetic field.

The tools developed in the prior art have disadvantages which limit their utility in nuclear magnetic resonance logging applications. Magnet designs of prior art tools do not simultaneously produce a highly axisymmetric static magnetic field with long straight contour lines in the resonance region of the formation under evaluation. These factors adversely affect the NMR measurement given the vertical motion of a wireline tool and the vertical and lateral motion of a logging-while-drilling tool.

SUMMARY OF THE INVENTION

The above disadvantages of the prior art are overcome by means of the subject invention for an apparatus and method for generating a substantially axisymmetric static magnetic field having long, straight contour lines in the resonance region. A wireline or logging-while-drilling apparatus within a borehole traversing an earth formation determines a formation characteristic by obtaining a nuclear magnetic resonance measurement. The apparatus produces a static magnetic field, $B_0$, into the formation such that the contour lines generated by the static magnetic field are substantially straight in the axial direction at the depth of investigation where the nuclear magnetic resonance measurement is obtained. An oscillating field, $B_1$, is produced in the same region of the formation as the static magnetic field to obtain the NMR measurement. The apparatus includes at least one magnetically permeable member for focusing the static magnetic field. The magnetically permeable member minimizes variations of the static magnetic field in the formation due to vertical motion of the apparatus while obtaining the nuclear magnetic resonance measurement. Further, the magnetically permeable member may minimize variations of the static magnetic field in the formation due to lateral motion of the apparatus while obtaining the nuclear magnetic resonance measurement. In addition, the magnetically permeable member can add significant, prepolarization by causing the $B_0$ field to have substantial magnitude well ahead of the actual region of investigation which can permit increased logging speed.

The static magnetic field is produced using either an axial, radial, or bobbin magnet design. For the axial design, the static magnetic field is produced by an upper magnet surrounding the carrying means and a lower magnet surrounding the carrying means and axially separated from the upper magnet by a distance such that the contour lines generated by the static magnetic field are substantially straight in the axial direction at the depth of investigation where the nuclear magnetic resonance measurement is obtained. The magnets are axially magnetized giving a radially polarized $B_0$ field in the region of investigation. At least one magnetically permeable member for shaping the static magnetic field is located between the lower magnet and the upper magnet. The static magnetic field has either a low gradient or a high gradient, depending on the separation of the magnets, at the depth of investigation where the nuclear magnetic resonance measurement is obtained.

For the radial design, the static magnetic field is produced by an annular cylindrical array of magnets surrounding the carrying means. The array of magnets comprises a plurality of segments, each segment is magnetized in a direction radially outward from and perpendicular to the longitudinal axis of the apparatus. The magnetically permeable member comprises a section of the carrying means, a chassis surrounding a section of the carrying means, or a combination of the chassis and the carrying means section.

For the bobbin design, the static magnetic field is produced by a plurality of geometrically and axisymmetric magnet rings surrounding the carrying means. The plurality of rings comprises an upper ring, a plurality of inner rings, and a lower ring. The radius of the upper and lower rings is greater then the radius of each inner ring. Each of the plurality of rings is axisymmetrically polarized and the direction of polarization for each ring differs progressively along the ring of magnets. The polarization direction of the upper ring is radially opposite to the polarization direction of the lower ring. The polarization of each inner ring changes progressively such that an angle between the polarization and a transverse radius vector varies linearly for each inner ring.

BRIEF DESCRIPTION OF THE DRAWINGS

The advantages of the present invention will become apparent from the following description of the accompanying drawings. It is to be understood that the drawings are to be used for the purpose of illustration only, and not as a definition of the invention.

In the drawings:

FIG. 1 illustrates a nuclear magnetic resonance logging-while-drilling tool;

FIG. 2 depicts the low gradient magnet design;

DETAILED DESCRIPTION OF THE PREFERRED EMBODIMENT

Figure 2A:
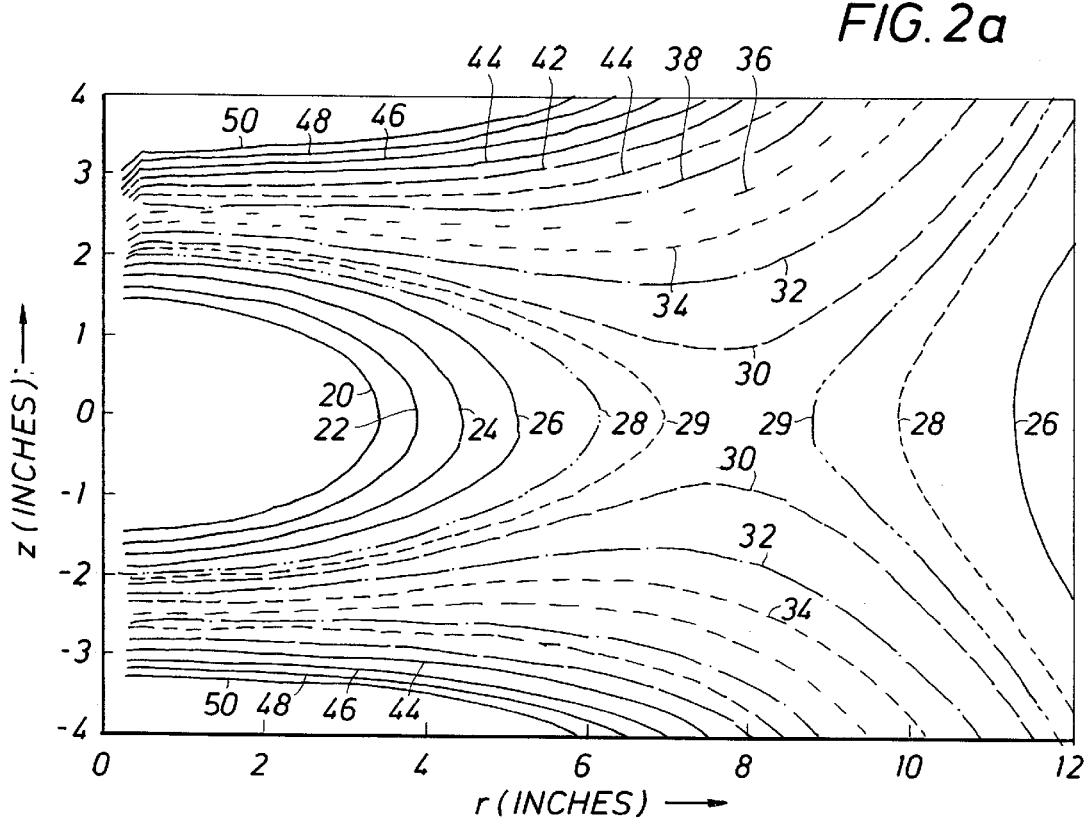
FIGS. 2a–2d illustrate the contour lines $|\vec{B}_0|$ corresponding to four low gradient magnet configurations.

Referring to FIG. 1, a nuclear magnetic resonance (NMR) logging-while-drilling tool 10 is illustrated. The tool 10 includes a drill bit 12, drill string 14, a magnet array 16, RF antenna 18, and electronic circuitry 20 housed within the drill collar 22. A means for drilling a borehole 24 in the formation comprises drill bit 12 and drill collar 22. The mud flow sleeve 28 defines a channel 30 for carrying the drilling fluid through the drill string 14. A drive mechanism 26 rotates the drill bit 12 and drill string 14. This drive mechanism is adequately described in U.S. Pat. No. 4,949,045 issued to Clark et al., the disclosure of which is incorporated by reference into this specification. However, it is also within contemplation of the subject invention to use a downhole mud motor placed in the drill string as the drive mechanism 26.

The magnetic field generated by magnet array 16 is focused by at least one magnetically permeable member 36 positioned inside the drill collar. With this arrangement, member 36 can extend a considerable length in the axial direction without decreasing the mechanical strength of the drill collar 22. Furthermore, if member 36 consists of a mechanically weak material, a separate, underlying mud flow sleeve 28 provides a degree of protection from the pressure, cuttings, and abrasion of drilling mud. Placement of member 36 outside the drill collar 22 would significantly weaken the mechanical integrity of the tool since that arrangement requires cutting a recessed area from the outside of the drill collar to accommodate member 36 thereby weakening collar 22 due to the section of drill collar between channel 30 and the recess having a decreased thickness in comparison to other sections of the drill collar. It is within contemplation of the subject invention that the magnetically permeable member 36 comprises a segment 38 of sleeve 28. In this case, an additional layer of space is not required inside the drill collar for member 36 and the available space is sufficient to accommodate a magnet array having a larger volume.

Low Gradient Design

Referring to FIG. 2, in a preferred embodiment of the invention, hereinafter referred to as the low gradient design, magnet array 16 comprises an upper magnet 32 axially separated from a lower magnet 34. The area between magnets 32, 34 is suitable for housing elements such as electronic components, an RF antenna, and other similar items. Both magnets 32, 34 surround sleeve 28. A magnetically permeable member 36 is positioned inside the drill collar 22 between the magnets 32, 34. Member 36 may consist of a single piece or a plurality of sections combined between the magnets. Member 36 is constructed of a suitable magnetically permeable material, such as ferrite, permeable steel or another alloy of iron and nickel, corrosion resistant permeable steel, or permeable steel having a structural role in the member design, such as 15-5 Ph stainless steel. The magnetically permeable member 36 focuses the magnetic field and either carries drilling fluid through the drill string or provides structural support to the drill collar. Further, member 36 improves the shape of the static magnetic field generated by magnets 32, 34 and minimizes variations of the static magnetic field due to vertical and lateral tool motion during the period of acquisition of the NMR signal. The segment 38 of sleeve 28 between magnets 32, 34 may comprise magnetically permeable member 36. In this case, the segments 40, 42 of sleeve 28 under magnets 32, 34 shall consist of a non-magnetic member. Alternatively, a magnetically permeable chassis 44 surrounding segment 38 defines member 36. In this case, segment 38 may consist of a magnetic or non-magnetic material. It is within contemplation of this invention to integrate chassis 44 and segment 38 to form member 36.

The magnets 32, 34 are polarized in a direction parallel to the longitudinal axis of the tool 10 with like magnetic poles facing each other. For each magnet 32, 34, the magnetic lines of induction travel outward from an end of the magnet 32, 34 into the formation to create a static field parallel to the axis of the tool 10 and travel inward to the other end of the magnet 32, 34. In the region between upper magnet 32 and lower magnet 34, the magnetic lines of induction travel from the center outward into the formation, creating a static field in the direction perpendicular to the axis of the tool 10. The magnetic lines of induction then travel inward symmetrically above the upper magnet 32 and below the lower magnet 34 and converge in the longitudinal direction inside sleeve 28. Because of the separation, the magnitude of the static magnetic field in the central region between the upper 32 and lower 34 magnet is relatively homogeneous. The amount of separation between the magnets 32, 34 is determined by selecting the requisite magnetic field strength and homogeneity characteristics. As the separation between the magnets 32, 34 decreases, the magnetic field becomes stronger and less homogeneous. Conversely, as the separation between the magnets 32, 34 increases, the magnetic field becomes weaker and more homogeneous.

FIGS. 2a–2d illustrate the contour lines of $|\vec{B}_0|$ corresponding to four configurations of upper 32 and lower 34 magnets. The configuration corresponding to FIG. 2a comprises a non-magnetically permeable member separating an upper 32 and lower 34 magnet by 25 inches. The configuration corresponding to FIG. 2b comprises a non-magnetically permeable member separating an upper 32 and lower 34 magnet by 18 inches. The configuration corresponding to FIG. 2c comprises a non-magnetically permeable member separating an upper 32 and lower 34 magnet by eight inches. The low gradient design, corresponding to FIG. 2d, comprises a magnetically permeable member 36 separating an upper 32 and lower 34 magnet by 25 inches. FIGS. 3a–3d represent the contour lines of the gradient $|\nabla \vec{B}_0|$ corresponding respectively to configurations illustrated in FIGS. 2a–2d.

Figure 3A:
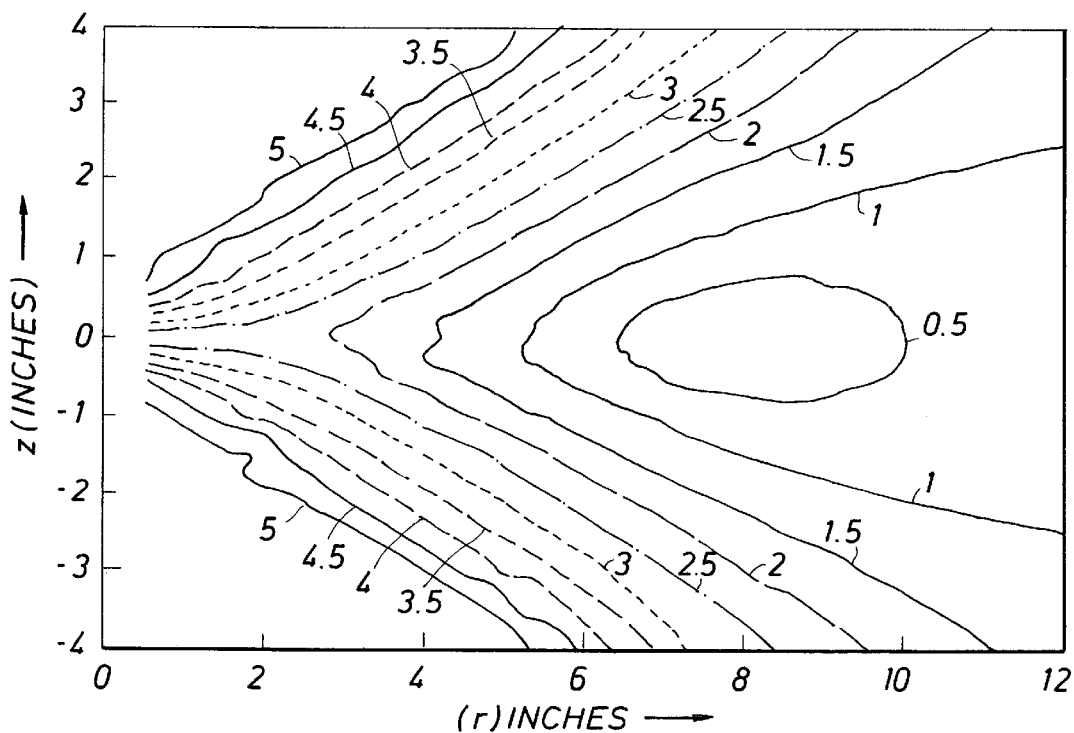
FIGS. 3a–3d represent the contour lines of the gradient $|\nabla \vec{B}_0|$ corresponding to four low gradient magnet configurations.
Figure 3B:
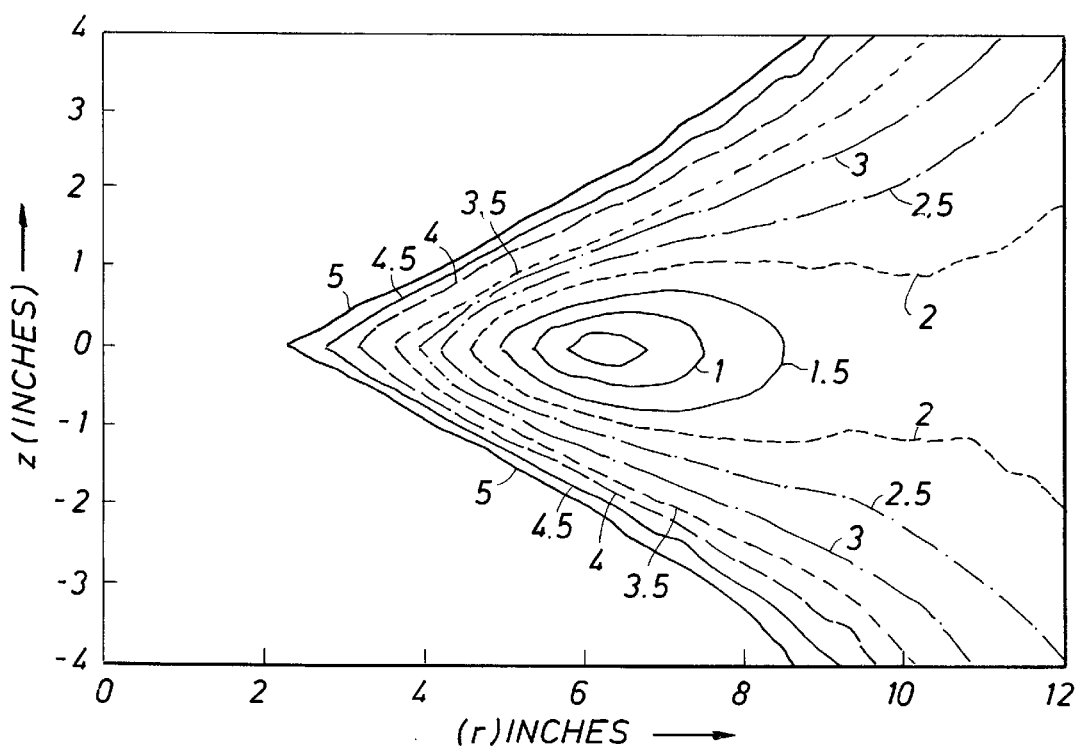
Figure 3C:
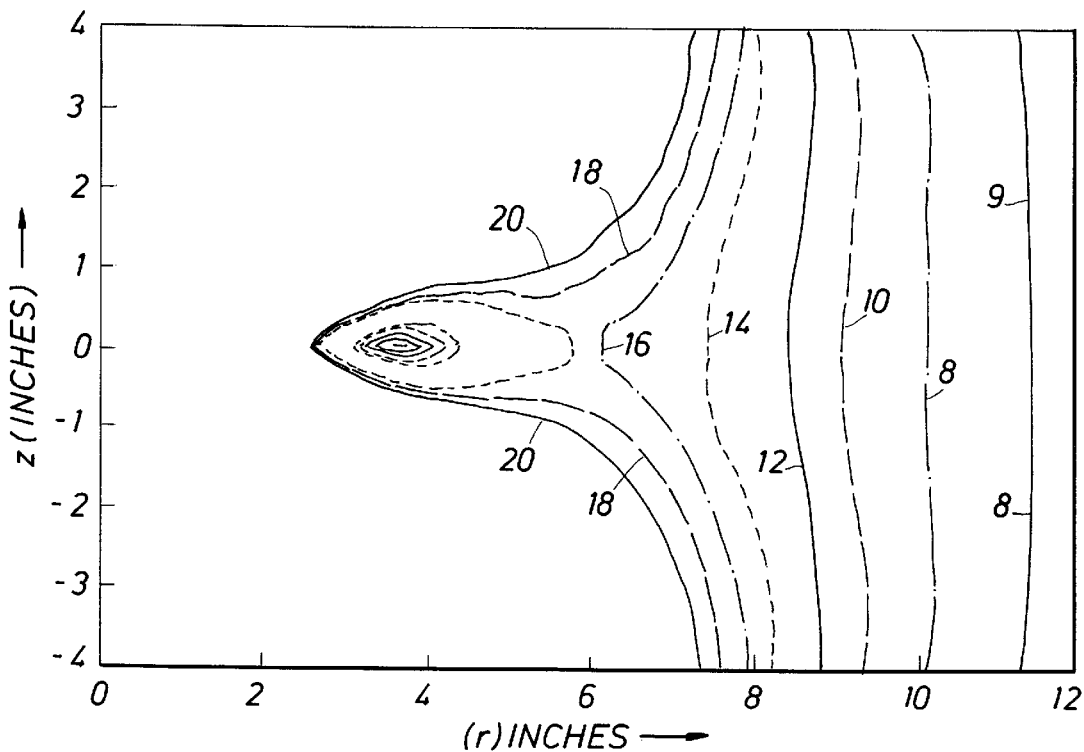
Figure 3D:
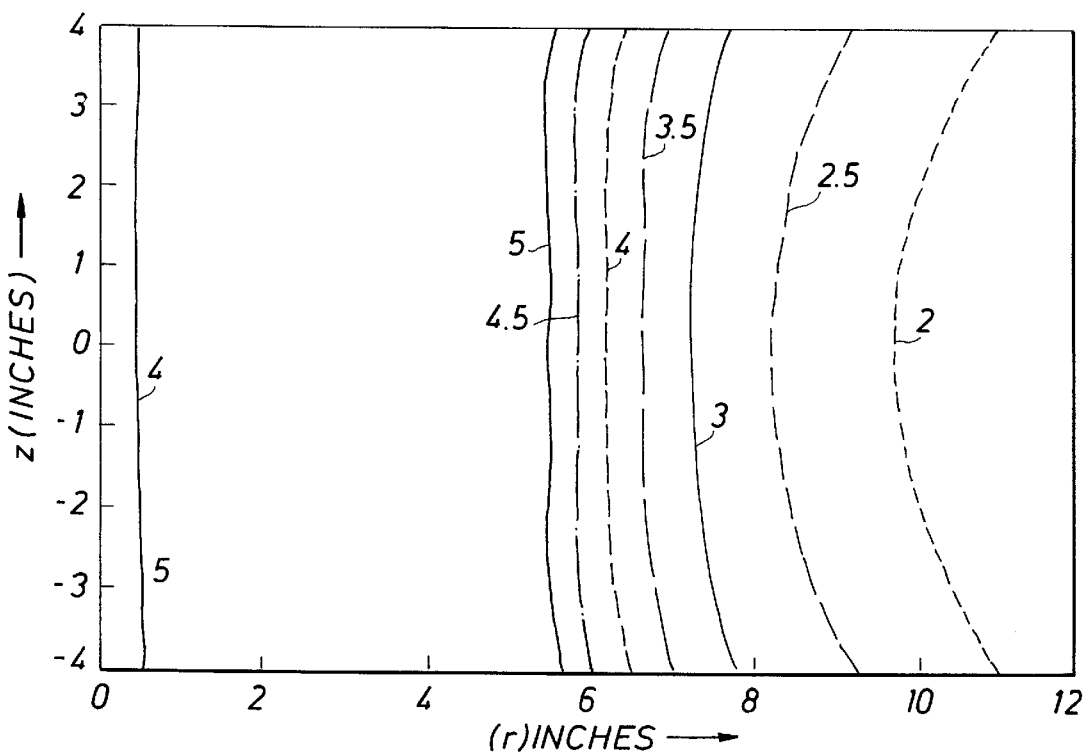

In the low gradient design, a significant portion of the magnetic flux is shunted by the magnetically permeable member 36 into the center of the tool 10. To illustrate, the magnitude of the $B_0$ field shown in FIG. 2d at a distance of approximately seven inches radially from the longitudinal axis of tool 10 is twice as large as the $B_0$ field shown in FIG. 2a which was generated by the same magnet configuration separated by a non-magnetically permeable member. Furthermore, the low gradient design produces a longer and more uniform extent of the static magnetic field in the axial direction. The NMR signal measured in this embodiment is substantially less sensitive to the vertical motion of the tool. Referring to FIG. 3d, with the low gradient design, a relatively small, approximately 3 Gauss/cm, gradient is measured at a distance of approximately seven inches radially from the longitudinal axis of tool. This low gradient results in a measured NMR signal which is substantially less sensitive to the lateral motion of the tool 10. Moreover, with the low gradient design, the proton rich borehole region surrounding the tool 10 will resonate only at frequencies higher than those being applied to the volume of investigation, i.e., there is no borehole signal. This is a characteristic of all embodiments of this invention. Other NMR sensitive nuclei found in drilling mud, such as sodium-23, resonate at significantly higher static magnetic field strengths than hydrogen when excited at the same RF frequency. These higher field strengths are not produced in the borehole region surrounding the tool or near the antenna where such unwanted signals could be detected. This is a characteristic of the axial magnet designs of this invention, including the high gradient design.

High Gradient Design

Figure 2B:
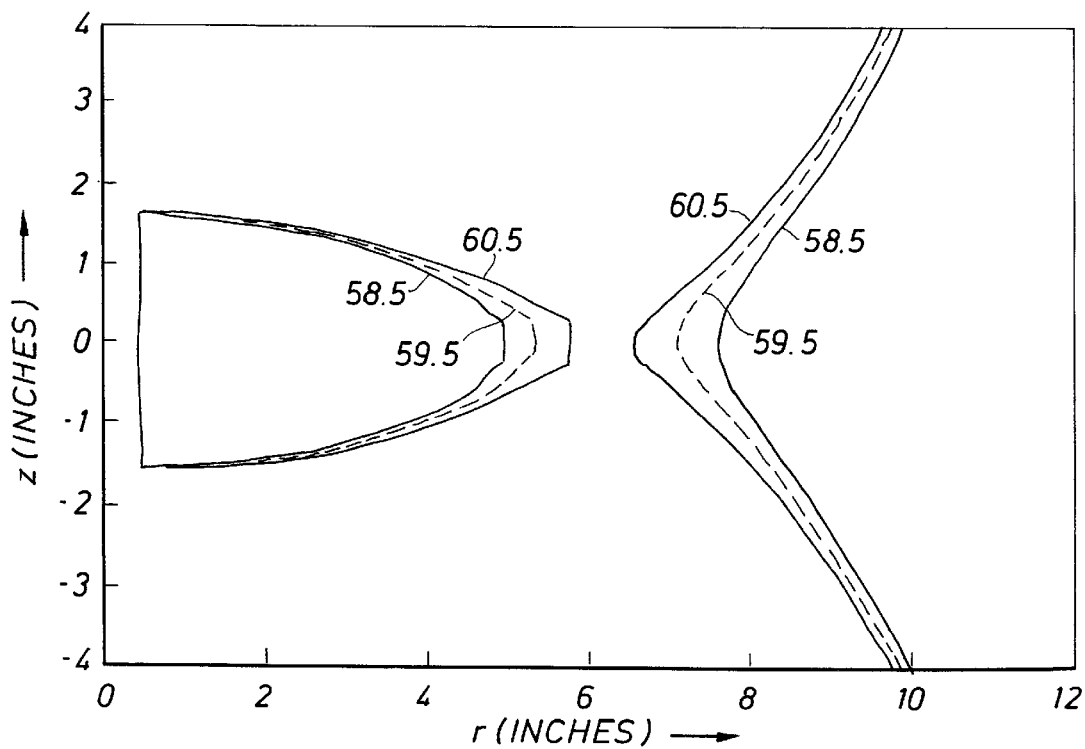

As previously described, with the low gradient design, a significant portion of the magnetic flux is shunted by the magnetically permeable member 36 into the center of the tool 10. Without the shunting of magnetically permeable member 36, a high gradient design is achieved by separating the upper 32 and lower 34 magnet to obtain the same $|\vec{B}_0|$ illustrated in FIG. 2d. As shown in FIG. 2b, a magnetic field strength, 60 Gauss, at a distance of approximately seven inches radially from the longitudinal axis of tool 10, is achieved by a non-magnetically permeable member separating the magnets 32, 34 by 18 inches. However, the shape of the volume of investigation in which the static magnetic field strength is in resonance with the RF frequency remains curved, and the field contour lines are relatively short in the axial direction. Furthermore, the receiver for detecting the NMR signal is sensitive to the borehole signal, as indicated by the two separate magnetic field regions shown in FIG. 2b.

Figure 2C:
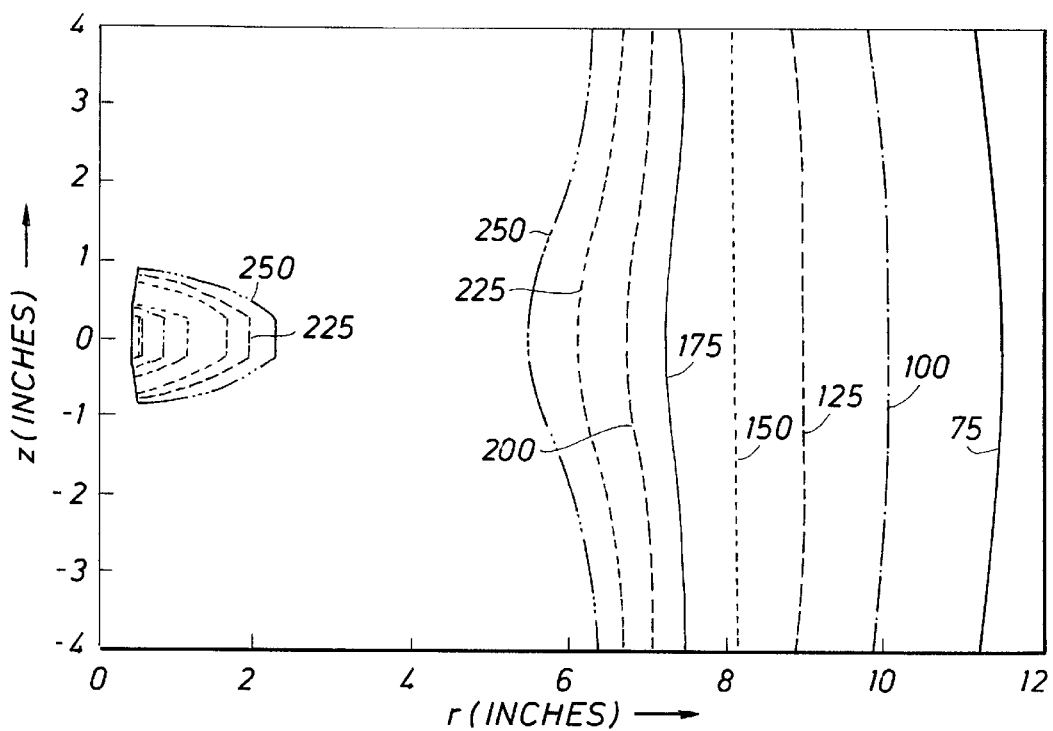
Figure 2D:
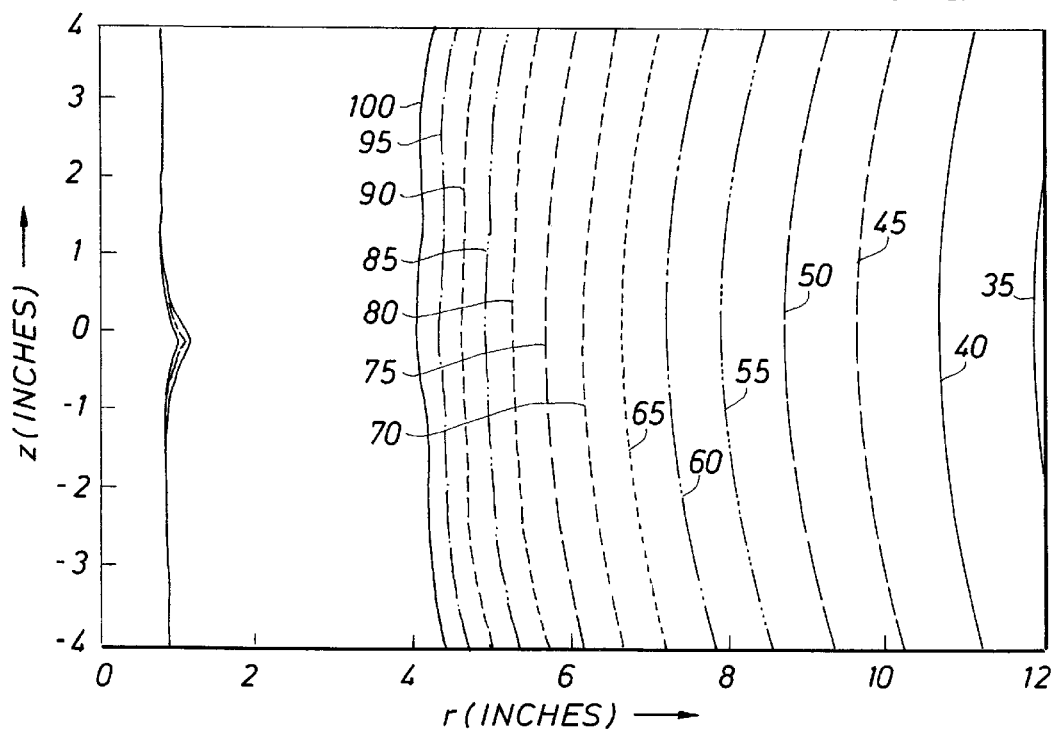

For a high gradient design using a non-magnetically permeable member, the curved shape of the volume of investigation and the borehole signal are overcome by decreasing the separation between magnets 32 and 34. As illustrated in FIG. 2c, if the magnet separation is decreased to approximately eight inches, the contour lines of the static magnetic field strength become straighter and the strength of $|\vec{B}_0|$ increases. However, the gradient $|\nabla \vec{B}_0|$ becomes larger, as illustrated in FIG. 3c, at a distance of approximately seven inches radially from the longitudinal axis of the tool. The contour lines of $|\nabla \vec{B}_0|$ are curved denoting variation of the gradient in the axial direction.

Figure 4:
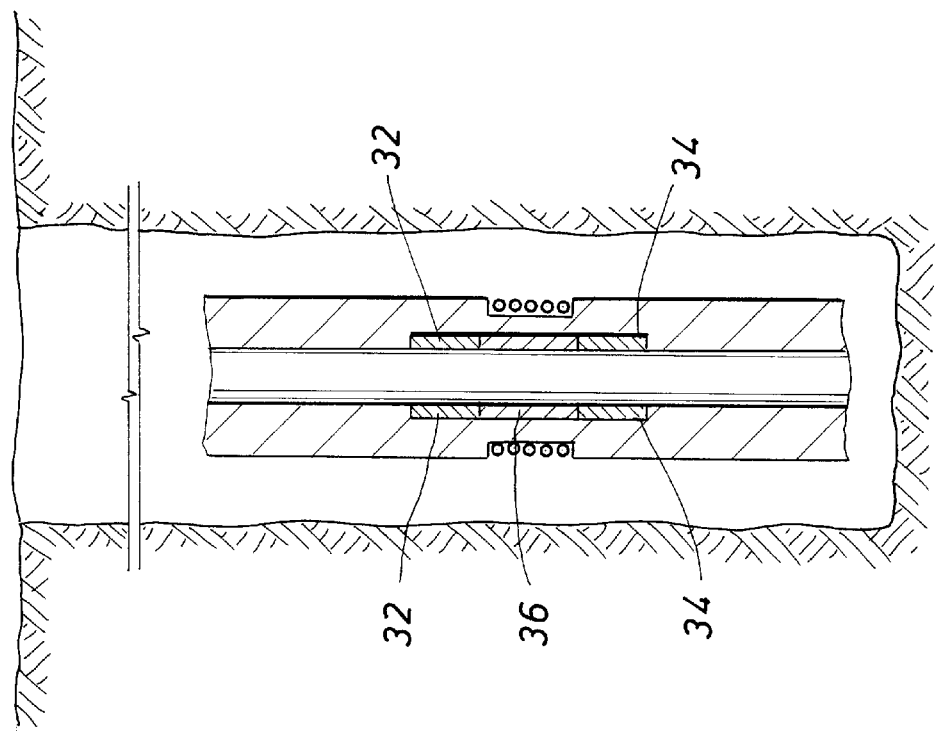
FIG. 4 depicts the high gradient magnet design.
Figure 4A:
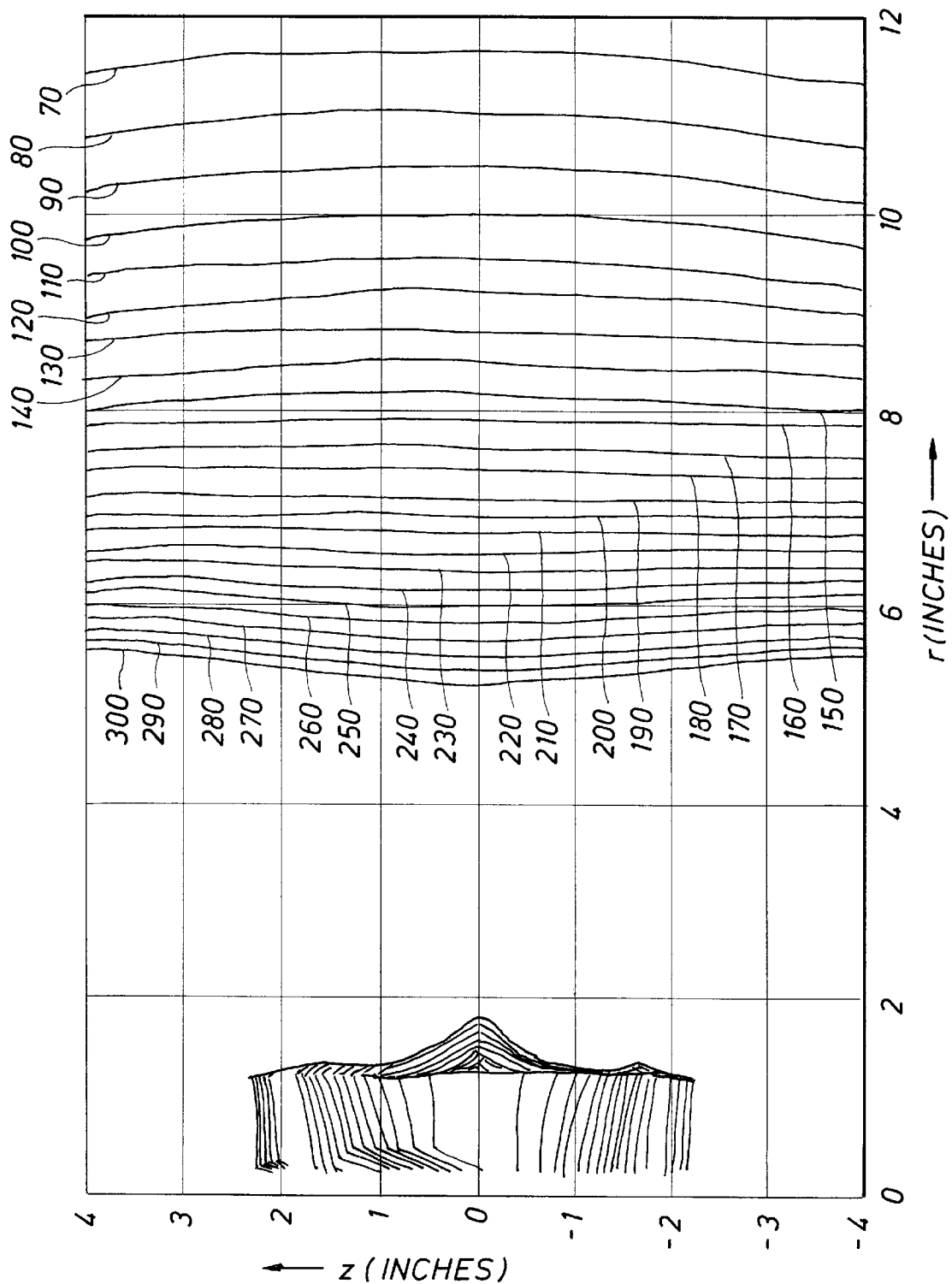
FIG. 4a represents the contour lines $|\vec{B}_0|$ corresponding to the high gradient magnet configuration.
Figure 4B:
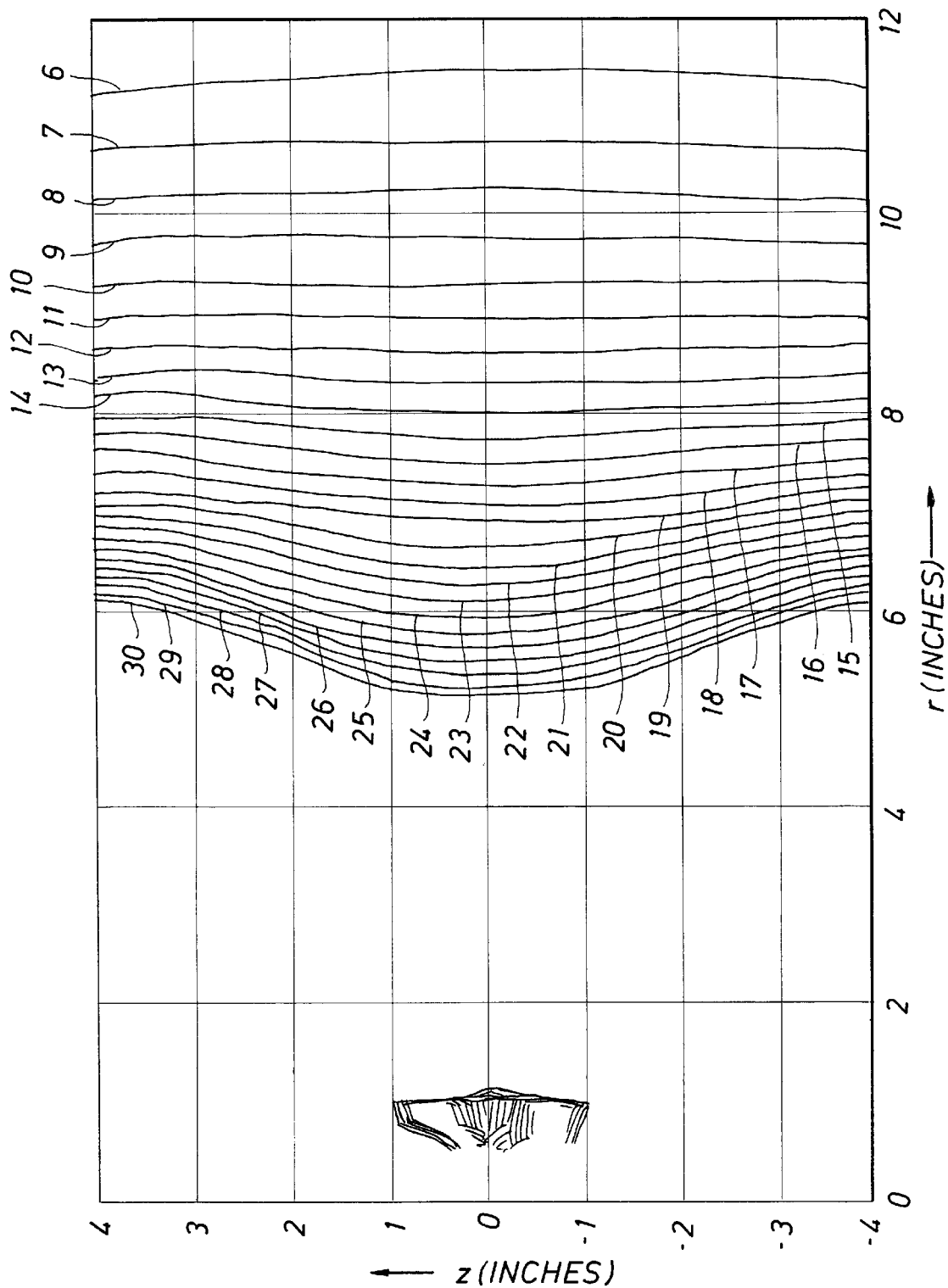
FIG. 4b represents the contour lines of the gradient $|\nabla \vec{B}_0|$ corresponding to the high gradient magnet configuration.

Referring to FIG. 4, the high gradient design is improved by inserting a magnetically permeable member 36 between magnets 32, 34. FIG. 4a represents contour lines of $|\vec{B}_0|$ corresponding to a configuration where magnetically permeable member 36 20 separates the upper 32 and lower 34 magnets by eight inches. The contour lines of FIG. 4a show less curvature in the axial direction than the contour lines of FIG. 2c. Also, as illustrated in FIG. 4b, the magnetically permeable member 36 produces a more constant gradient $|\nabla \vec{B}_0|$ in the axial direction.

Bobbin Design

Figure 5:
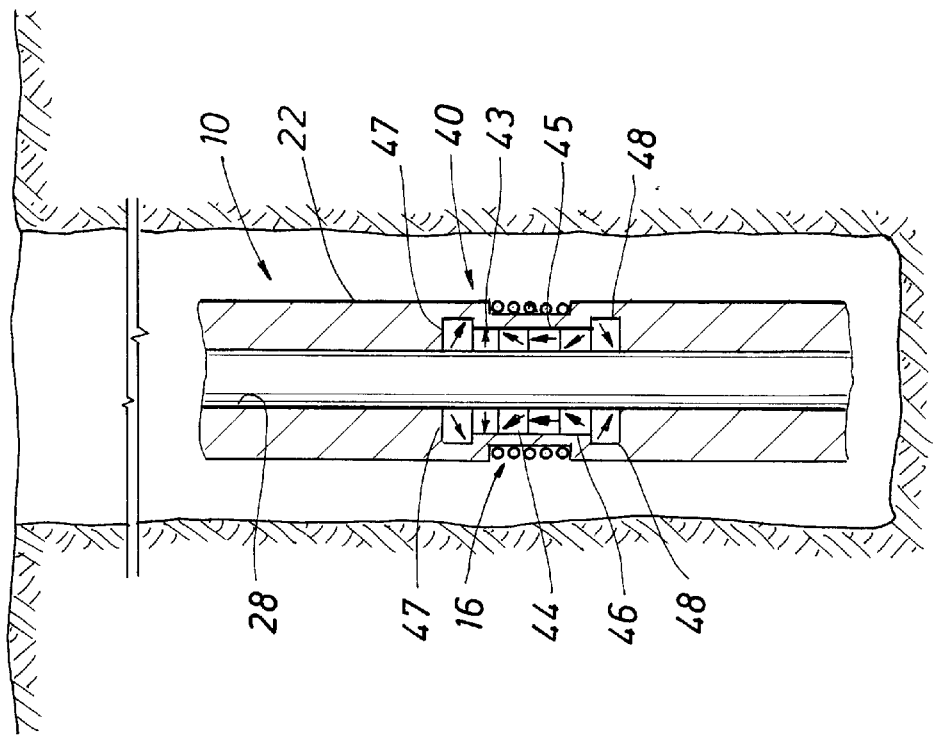
FIG. 5 depicts the bobbin magnet design.

Referring to FIG. 5, in a second embodiment of the invention, hereinafter referred to as the bobbin design, magnet array 16 comprises a geometrically and magnetically axisymmetric array of magnets 40 surrounding sleeve 28. Preferably, sleeve 28 is constructed of a suitable magnetically permeable material, such as ferrite, permeable steel or another alloy of iron and nickel, corrosion resistant permeable steel, or permeable steel having a structural role in the member design, such as 15-5 Ph stainless steel. However, it is within contemplation of the subject invention to have a non-magnetically permeable sleeve. The magnet array 40 comprises a ring of magnets 43, 44, 45, 46, 47, and 48. The radius of the uppermost ring 47 and the lowermost ring 48 is greater than the plurality of rings 43, 44, 45, 46 defining a central array 42. The area between rings 47 and 48 can accommodate a deep RF antenna mounted on the drill collar 22.

With the bobbin design, each ring of the array 40 is axisymmerically polarized but the directions of polarization differ progressively along the array 40. The polarization of the uppermost ring 47 and the lowermost ring 48 are oriented such that their respective lines of extension intersect in the NMR measurement zone of investigation in the formation. Consequently, the orientations of the magnetization of rings 47 and 48 are radially oppose to each other. By way of example FIG. 5 illustrates the orientation of the magnetization of ring 47 directed outward into the formation and the orientation of the magnetization of ring 48 directed inward. Progressing away from uppermost ring 47, the polarization of each ring 43, 44, 45, and 46 is tipped and changes progressively in a manner such that the angle between the polarization and the transverse radius vector varies linearly for each ring in the central array. With the bobbin design, the path of magnetic lines of induction travels outward, away from the upper ring 47, into the formation to create a static magnetic field parallel to the axis of the borehole at the center of the tool 10 and travels inward, towards the lower ring 48.

Figure 5A:
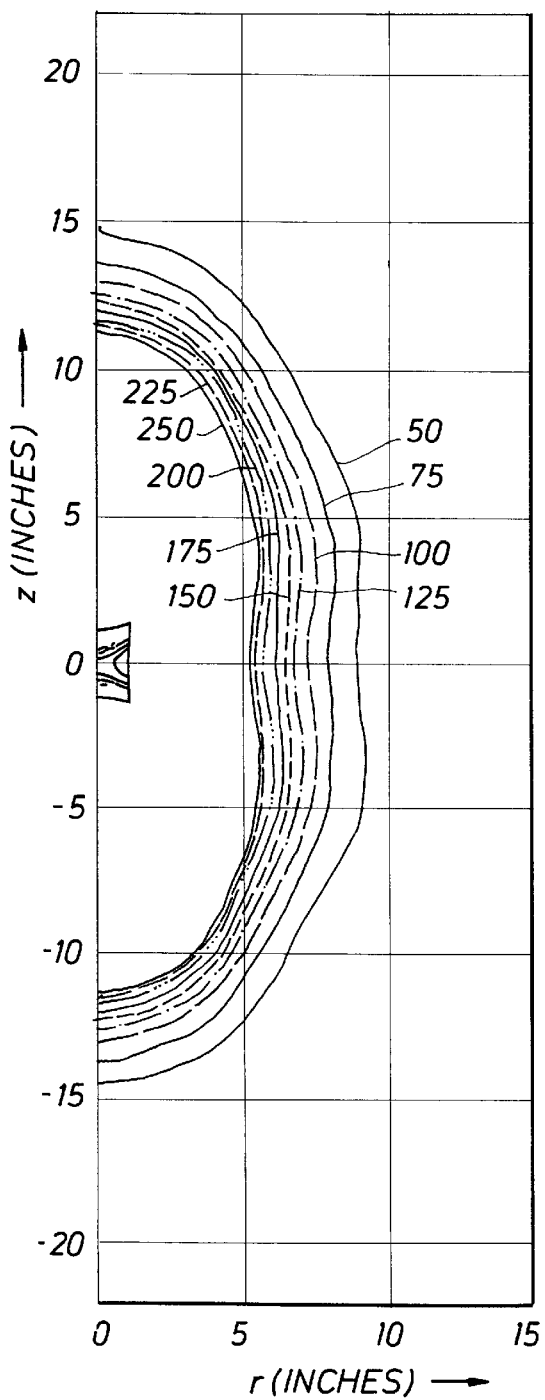
FIG. 5a represents the contour lines $|\vec{B}_0|$ corresponding to the bobbin magnet configuration with a non-magnetically permeable member.
Figure 5B:
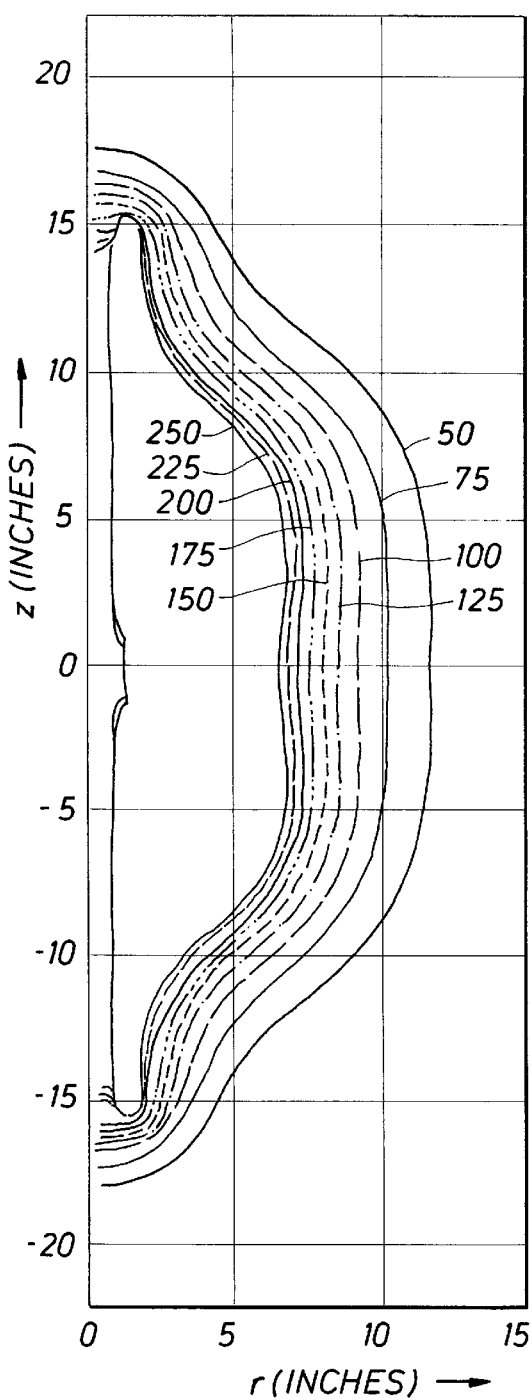
FIG. 5b represents the contour lines $|\vec{B}_0|$ corresponding to the bobbin magnet configuration with a magnetically permeable member.

Referring to FIG. 5b, the magnet configuration depicted in FIG. 5, used in conjunction with a magnetically permeable sleeve 28, produces a longer and more uniform static field in the axial direction. The contour lines of $|\vec{B}_0|$ depicted in FIG. 5b are straighter in the middle of the tool 10 than the contour lines of $|\vec{B}_0|$ illustrated in FIG. 5a. Also, the magnetically permeable sleeve of the subject invention permits the magnet array 40 to generate a stronger field at the same location in the formation in comparison to the magnet array 40 surrounding a non-magnetically permeable sleeve. The increased strength of the static field significantly improves the signal-to-noise ratio and enhances the depth of investigation.

Radial Design

Figure 6:
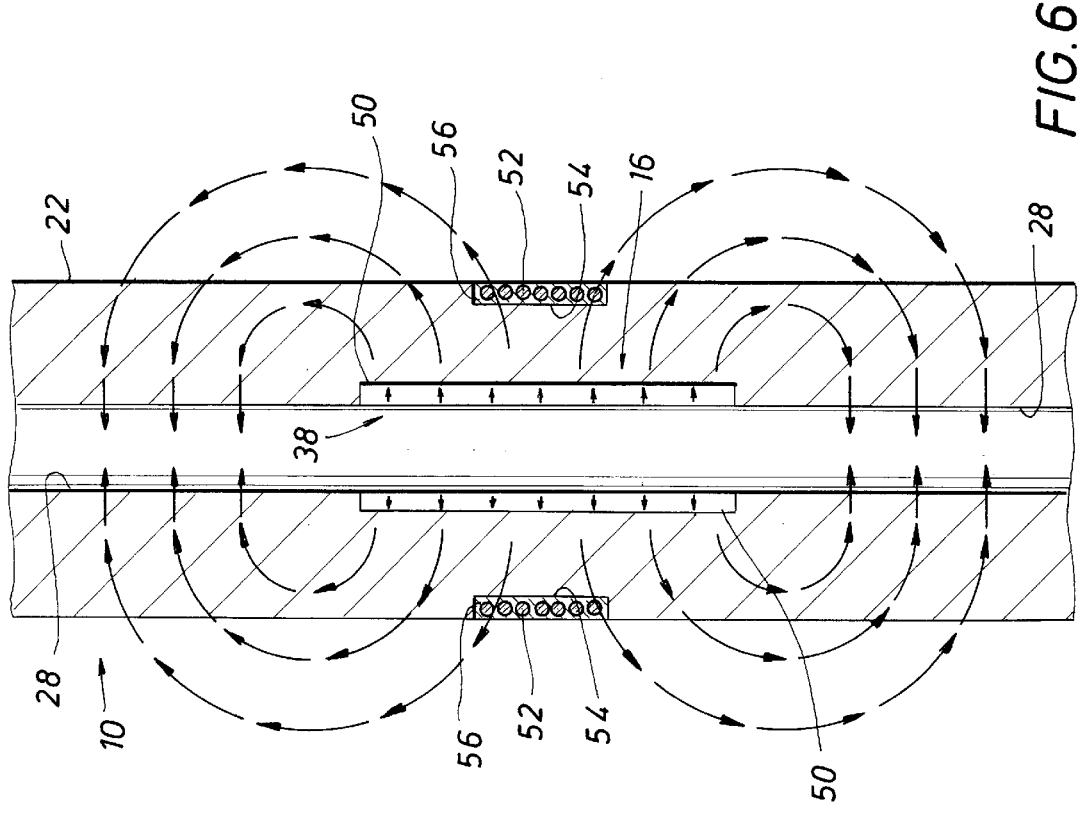
FIG. 6 depicts the radial magnet design.

Referring to FIG. 6, in a third embodiment of the invention, hereinafter referred to as the radial design, magnet array 16 comprises an annular cylindrical magnet array 50 surrounding a segment 38 of sleeve 28. The magnet array 50 is comprised of a plurality of segments, each segment is magnetized radially, that is, outward from the longitudinal axis of the tool 10. Such a magnet array is described in U.S. Pat. No. 4,717,876 to Masi et al., for example. An antenna 52 is mounted in an exterior recess 54 of the drill collar 22. A non-conductive, magnetically permeable layer of material 56, such as ferrite, fills recess 54. The antenna 52 also surrounds sleeve 28. The RF magnetic field, $B_1$, generated by current flowing through antenna 52 has field directions substantially parallel to the longitudinal. axis of the tool 10. Alternatively, the RF magnetic field, $B_1$, is generated by an array of antennas and $B_1$ extends azimuthally about the longitudinal axis of the tool 10.

Figure 6A:
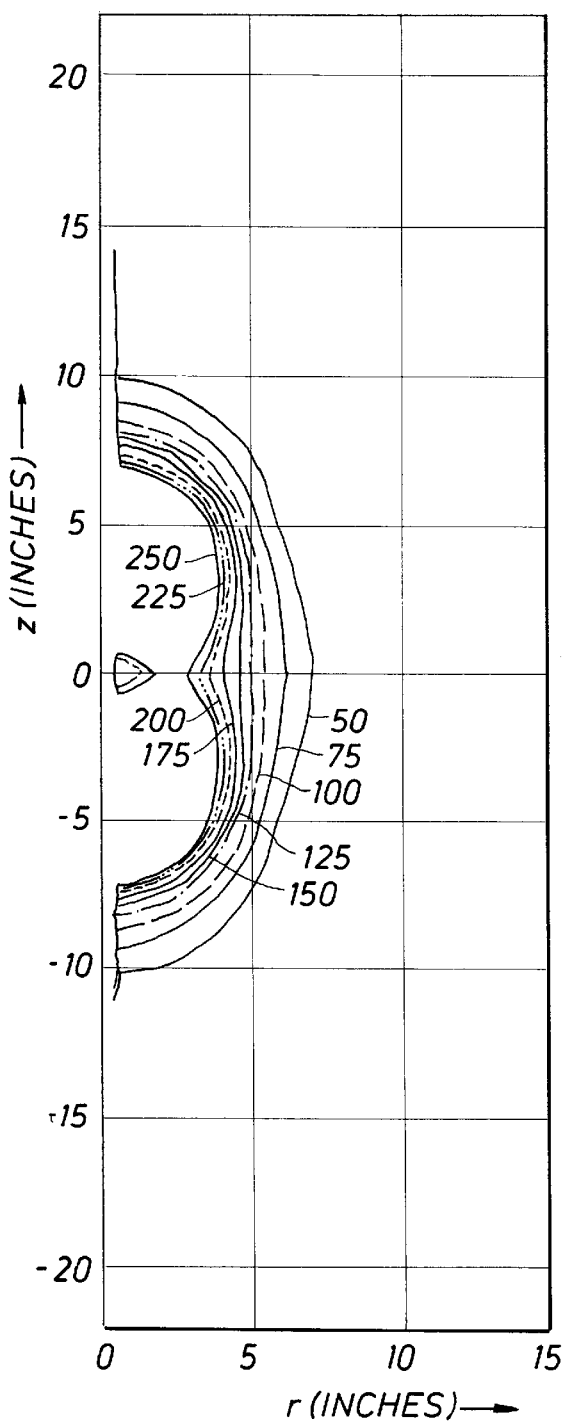
FIG. 6a represents the contour lines $|\vec{B}_0|$ corresponding to the radial magnet configuration with a non-magnetically permeable member.
Figure 6B:
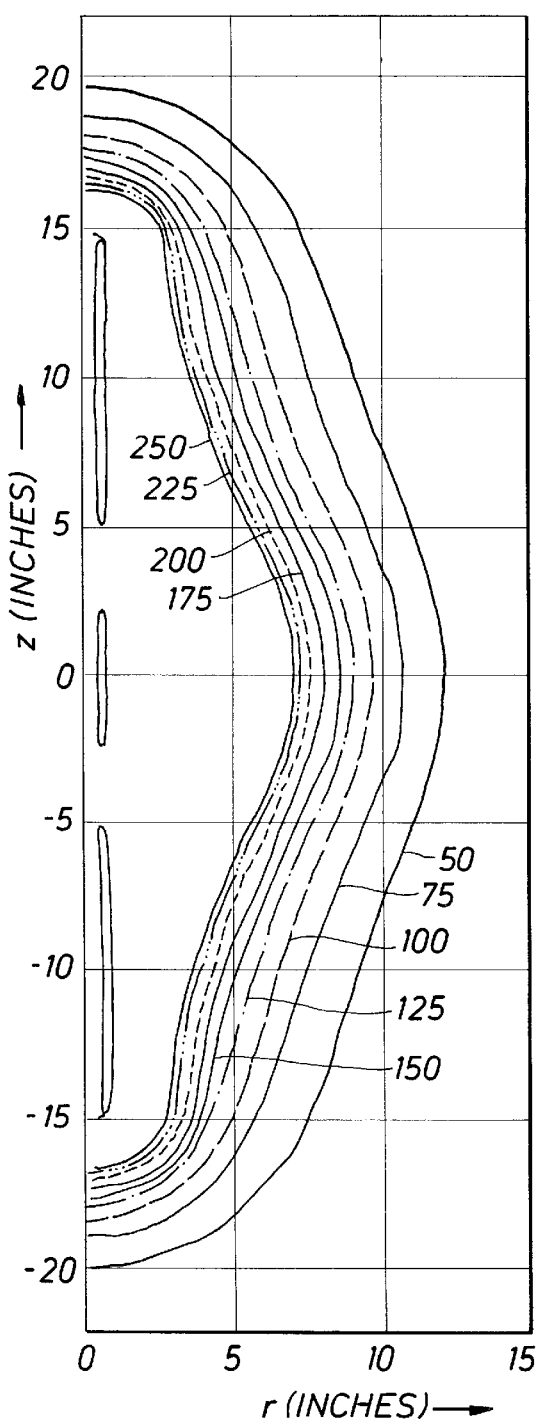
FIG. 6b represents the contour lines $|\vec{B}_0|$ corresponding to the radial magnet configuration with a. magnetically permeable member.

Still referring to FIG. 6, magnetically permeable member is comprised of segment 38. Similar to the low gradient design, a chassis (not shown) surrounding segment 38 may define the permeable member. For illustrative purposes only, the radial design described herein may include a magnetically permeable member consisting of segment 39, which is constructed of a suitable magnetically permeable material such as ferrite, permeable steel or another alloy of iron and nickel, corrosion resistant permeable steel, or permeable steel having a structural role in the sleeve design, such as 15-5 Ph stainless steel. The use of a magnetically permeable material for the segment 38 improves the shape of the static magnetic field generated by magnet array 50 and minimizes variations of the static magnetic field due to vertical tool motion during the period of acquisition of the NMR signal. The direction of the static field is illustrated by vectors. The path of the magnetic lines of induction travels from the central section of the magnet array 50 outward into the formation creating a static magnetic field in the direction perpendicular to the borehole axis, travels inward systematically above and below the magnet array 50 through segment 38, and then converges in the longitudinal direction inside sleeve 28, returning to the central section of the magnet array 50. The magnetically permeable material forces the return magnetic lines of induction to be more orthogonal to the axial direction when crossing the outer surface of segment 38. FIGS. 6a and 6b compare the field strength of the array of magnets 50 surrounding a non-magnetically permeable segment 38 versus the field strength of the array of magnets 50 surrounding a magnetically permeable segment 38.

Referring to FIG. 6a, with a non-magnetically permeable segment 38 (see FIG. 6), the magnetic energy is primarily concentrated at the extremities of the cylindrical array of magnets 50 (see FIG. 6). This heterogeneity characteristic of $B_0$ extends into the surrounding formation. The portions of the static field near the ends of the array (see 50 in FIG. 6) are larger than the field located in the middle of the tool 10. The shape of the formation volume in which the static magnetic field strength is in resonance with the RF frequency is curved, and the field contour lines are relatively short in the axial direction.

Referring to FIG. 6b, with a magnetically permeable segment 38 of sleeve 28 (see FIG. 6), a longer and more uniform static field is generated in the axial direction. The contour lines of $|\vec{B}_0|$ depicted in FIG. 6b are straighter in the middle of the tool 10 than the contour lines of $|\vec{B}_0|$ illustrated in FIG. 6a. The magnetically permeable segment 38 of sleeve 28 serves a dual purpose of focusing the magnetic field and carrying the drilling fluid through the drill string. Also the magnetically permeable segment 38 of sleeve 23 of the subject invention permits the magnet array 50 (see FIG. 6) to generate a stronger field at the same location in the formation in comparison to the magnet array 50 surrounding a non-magnetically permeable sleeve 28. For example, as illustrated in FIG. 6a, the magnetic field strength is 50 Gauss where r=6" and z=5". In contrast, as illustrated in FIG. 6b, with a magnetically permeable segment 38 of sleeve 28. the magnetic field strength increases to 200 Gauss where r=6" and z=5". The increased strength of the static field significantly improves the signal-to-noise ratio of the NMR measurement and enhances the depth of measurement investigation.

Figure 7:
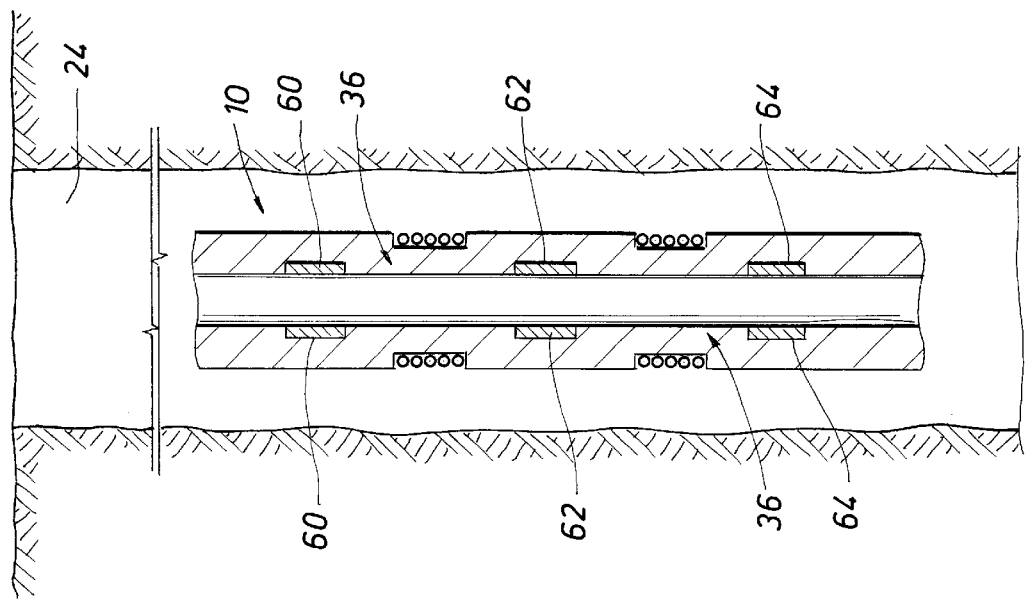
FIG. 7 depicts a combination magnet arrangement using three magnets.
Figure 7A:
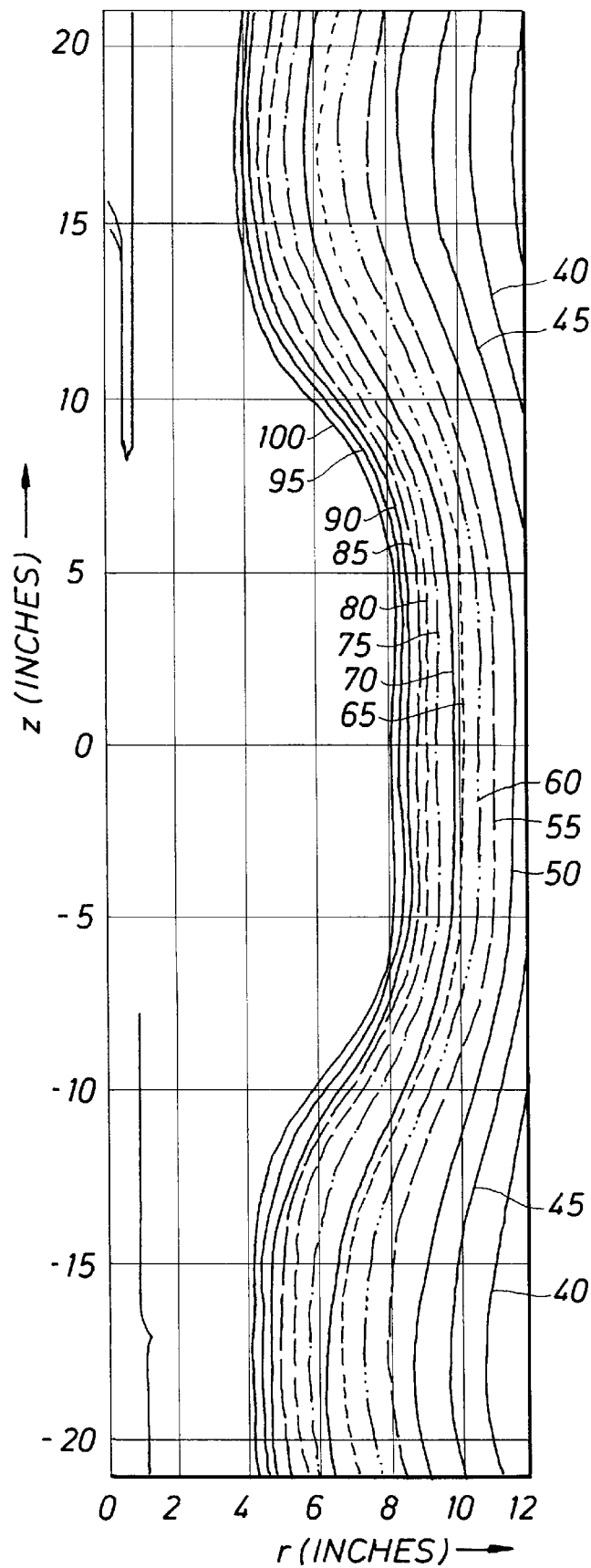
FIG. 7a represents the contour lines $|\vec{B}_0|$ corresponding to a combination low gradient-low gradient magnet arrangement.

It is within contemplation of the subject invention to generate a static magnetic field by combining N+1 magnet arrays to obtain at least N regions of investigation in the formation, The combinations contemplated by this invention include, but are not limited to, a low gradient-low gradient, high gradient-high gradient, high gradient-low gradient, or low gradient-high gradient combination of arrays. By way of example, FIG. 7 illustrates a first low gradient magnet array in combination with a second low gradient magnet array. In the region between upper magnet 60 and central magnet 62, the magnetic lines of induction travel from the center outward into formation creating a first static field in the direction perpendicular to the axis of the tool to 10. In the region between central magnet 62 and lower magnet 64, the magnetic lines of induction travel from the center outward into formation creating a second static field in the direction perpendicular to the axis of the tool 10. FIG. 7a illustrates the contour line of $|\vec{B}_0|$ corresponding to a configuration where a first magnetically permeable member separates upper magnet 60 and central magnet 62 by approximately 25 inches and a second magnetically permeable member separates central magnet 62 and lower magnet 64 by approximately 25 inches.

The low gradient, high gradient, bobbin, axial, and radial magnet designs of the present invention are also useful in a wireline logging tool application. Sleeve 28 would define a tubular member within the wireline tool which provides structural strength to the tool. Where sleeve 28 is the magnetically permeable member, the sleeve is designed to withstand substantial axial forces exerted on the tool during fishing operations. If sleeve 28 is the magnetically permeable member, the sleeve can be used for magnetic shielding of electronics, such as electromagnetic relays, that must be within the high magnetic field region produced by the nearby magnets. Moreover, member 36 can be used for the magnetic shielding.

The foregoing description of the preferred and alternate embodiments of the present invention has been presented for purposes of illustration and description. It is not intended to be exhaustive nor to limit the invention to the precise form disclosed. Obviously, many modifications and variations will be apparent to those skilled in the art. The embodiments were chosen and described in order to best explain the principles of the invention and its practical application thereby enabling others skilled in the art to understand the invention for various embodiments and with various modifications as are suited to the particular use contemplated. It is intended that the scope of the invention be defined by the accompanying claims and their equivalents.

What I claim is:

1. An apparatus for generating a magnetic field, comprising:
   a) a drilling means for drilling a borehole into a formation;
   b) a carrying means for carrying drilling fluid through the drilling means; and
   c) a measuring means, connected to the drilling means, for making nuclear magnetic resonance measurements while the borehole is being drilled, the measuring means comprising:
      i) a static magnetic field producing means for producing a substantially axisymmetric static magnetic field through the drilling means and into the formation, the static magnetic field producing means comprising:
         a) an axially magnetized upper magnet surrounding the carrying means; and
         b) an axially magnetized lower magnet surrounding the carrying means and axially separated from the upper magnet by a distance such that contour lines generated by the substantially axisymmetric static magnetic field are substantially straight in an axial direction at a depth of investigation where the nuclear magnetic resonance measurements are made; and
      ii) a means for producing an oscillating field in the formation.

2. The apparatus of claim 1 further comprising at least one magnetically permeable member for shaping the substantially axisymmetric static magnetic field, the at least one magnetically permeable member being located within the drilling means between the lower magnet and the upper magnet.

3. The apparatus of claim 2 wherein the upper magnet, the lower magnet, and the at least one magnetically permeable member are so arranged that the substantially axisymmetric static magnetic field, at the depth of investigation where the nuclear magnetic resonance measurements are made, has a low gradient in a direction perpendicular to an axial direction along the borehole.

4. The apparatus of claim 2 wherein the at least one magnetically permeable member comprises a section of the carrying means.

5. The apparatus of claim 4 wherein the at least one magnetically permeable member comprises a chassis surrounding the section of the carrying means.

6. The apparatus of claim 2 wherein the at least one magnetically permeable member comprises a chassis surrounding the carrying means.

7. The apparatus of claim 1 further comprising a region between the upper magnet and the lower magnet for locating electronics.

8. An apparatus for generating a magnetic fields comprising:
   a) a housing;
   b) a measuring means, located inside the housing for making nuclear magnetic resonance measurements, the measuring means comprising:
      i) a means for producing a substantially axisymmetric static magnetic field through the housing and into a formation such that contour lines generated by the substantially axisymmetric static magnetic field are substantially straight in an axial direction at a depth of investigation where the nuclear magnetic resonance measurements are made; and
      ii) a means for producing an oscillating field in the formation; and
   c) at least one magnetically permeable member for shaping the substantially axisymmetric static magnetic field.

9. The apparatus of claim 8 wherein the means for producing the substantially axisymmetric static magnetic field comprises:
   a) an axially magnetized upper magnet; and
   b) an axially magnetized lower magnet axially separated from the upper magnet by a distance such that the contour lines generated by the substantially axisymmetric static magnetic field are substantially straight in an axial direction.

10. The apparatus of claim 9 wherein the upper magnet, the lower magnet, and the at least one magnetically permeable member are so arranged that the substantially axisymmetric static magnetic field, at the depth of investigation where the nuclear magnetic resonance measurements are made, has a low gradient in a direction perpendicular to an axial direction along the borehole.

11. An apparatus for generating a magnetic field, comprising;
   a) a drilling means for drilling a borehole into a formation;
   b) a carrying means for carrying drilling fluid through the drilling means;
   c) a measuring means, connected to the drilling means, for making nuclear magnetic resonance measurements while the borehole is being drilled, the measuring means comprising:
      i) means for producing at last one substantially axisymmetric static magnetic field through the drilling means and into the formation at a plurality of regions of investigation where the nuclear magnetic resonance measurements are made, and such that contour lines generated by at least one substantially axisymmetric static magnetic field are substantially straight in an axial direction; and ii) means for producing an oscillating field in the formation; and d) at least one magnetically permeable member located inside the drilling means for shaping the at least one substantially axisymmetric static magnetic field.

12. The apparatus of claim 11 wherein the means for producing the at least one substantially axisymmetric static magnetic field comprises means for producing a first static magnetic field which comprises an axially magnetized upper magnet surrounding the carrying means and an axially magnetized central magnet surrounding the carrying means and axially separated from the upper magnet by a first distance.

13. The apparatus of claim 12 wherein the means for producing the at least one substantially axisymmetric static magnetic field comprises means for producing a second static magnetic field which comprises the axially magnetized central magnet surrounding the carrying means and an axially magnetized lower magnet surrounding the carrying means and axially separated from the central magnet by a second distance.

14. The apparatus of claim 13 wherein the first distance between the upper magnet and the central magnet in the means for producing the first static magnetic filed is such that the first static magnetic field, at a first region of investigation where the nuclear magnetic resonance measurements are made, has a low gradient in a direction perpendicular to an axial direction along the borehole.

15. The apparatus of claim 14 wherein the second distance between the central magnet and the lower magnet in the means for producing the second static magnetic field is such that the second static magnetic field, at a second region of investigation where the nuclear magnetic resonance measurements are made, has a low gradient in a direction perpendicular to an axial direction along the borehole.

16. An apparatus for eating a magnetic field, comprising:

a) a housing;

b) a measuring means, located inside the housing, for making nuclear magnetic resonance measurements, the measuring means comprising:

i) means for producing at least one substantially axisymmetric static magnetic field through the housing and into a formation at a plurality of regions of investigation where the nuclear magnetic resonance measurements are made and such that contour lines generated by the at least one substantially axisymmetric static magic field are substantially straight in an axial direction; and ii) means for producing an oscillating field in the formation; and c) at least one magnetically permeable member for shaping the at least one substantially axisymmetric static magnetic field, the at least one magnetically permeable member being disposed within the housing.

17. The apparatus of claim 16 wherein the means for producing the at least one substantially axisymmetric static magnetic field comprises means or producing a first static magnetic field which comprises an axially magnetized upper magnet surrounding the at least one magnetically permeable member and an axially magnetized central magnet surrounding the at least one magnetically permeable member and axially separated from the upper magnet by a fist distance.

18. The apparatus of claim 17 wherein the means for producing the at least one substantially axisymmetric static magnetic field comprises means for producing a second static magnetic field which comprises the axially magnetized central magnet surrounding the at least at one magnetically permeable member and an axially magnetized lower magnet surrounding the at least one magnetically permeable member and axially separated from the central magnet by a second distance.

19. The apparatus of claim 18 wherein the upper magnet and the central magnet in the means for producing the first static magnetic field are so spaced apart that the first italic magnetic field, at a first region of investigation where the nuclear magnetic resonance measurements are made, has a low gradient in a direction perpendicular to the axial direction.

20. The apparatus of claim 18 wherein the central magnet and the lower magnet in the means for producing the second static magnetic field are so spaced apart that the second static magnetic field, at a second region of investigation where the nuclear magnetic resonance measurements are made, has a low gradient in a direction perpendicular to the axial direction.

21. The apparatus of claim 18 wherein the central magnet and the lower magnet in the means for producing the second static magnetic field are so spaced apart that the second static magnetic field, at a second region of investigation where the nuclear magnetic resonance measurements are made has a high gradient in a direction perpendicular to the axial direction.

22. The apparatus of claim 18 wherein the upper magnet and the central magnet in the means for producing the first static magnetic field are so spaced apart that the first static magnetic field, at a first region of investigation where the nuclear magnetic resonance measurements are made, has a high gradient in a direction perpendicular to the axial direction.

23. An apparatus for nuclear magnetic resonance measurements in a formation penetrated by a borehole, comprising;

a) an axially magnetized upper magnet;

b) an axially magnetized lower magnet, wherein the lower magnet is axially spaced at a distance from the upper such that a static magnetic field generated by the upper magnet and the lower magnet is substantially axisymmetric, and contour lines of the static magnetic field at a region where the nuclear magnetic resonance measurements are made are substantially straight in a direction along an axial direction of the borehole; and c) at least one antenna for generating an oscillating magnetic field in the formation, wherein the at least one antenna is disposed between the upper magnet and the lower magnet.

24. The apparatus of claim 23, further comprising at least one magnetically permeable member disposed between the upper magnet and the lower magnet.

25. The apparatus of claim 24, wherein the distance between the upper magnet and the lower magnet is such that the static magnetic field at the region where the nuclear magnetic resonance measurements are made has a low gradient in a direction perpendicular to the axial direction of the borehole.

26. The apparatus of claim 23, wherein the distance between the upper magnet and the lower magnet is such that the static magnetic field at the region where the nuclear magnetic resonance measurements are made has a high gradient in a direction perpendicular to the axial direction of the borehole.

27. The apparatus of claim 26, further comprising at least one magnetically permeable member disposed between the upper magnet and the lower magnet.

28. An apparatus for nuclear magnetic resonance measurements in a formation penetrated by a borehole comprising;

b) a plurality of axially-magnetized magnets disposed spaced-apart along an axis, forming at least one inter-magnet space, wherein a static magnetic field generated by the plurality of axially-magnetized magnets is substantially axisymmetric, the static magnetic field at a region where the nuclear magnetic resonance measurements are made is substantially straight in a direction along an axial direction of the borehole; and c) at least one antenna disposed in the at least one inter-magnet space.

29. The apparatus of claim 28, further comprising at least one magnetically permeable member disposed in the at least one inter-magnet space.

30. The apparatus of claim 29, wherein at least two neighboring magnets are so spaced that a static magnetic field generated by the two neighboring magnets at the region where the nuclear magnetic resonance measurements are made has a low gradient in a direction perpendicular to the axial direction of the borehole.

31. The apparatus of claim 28, wherein at least two neighboring magnets are so spaced that a static magnetic field generated by the two neighboring magnets at the region where the nuclear magnetic resonance measurements are made has a high gradient in a direction perpendicular to the axial direction of the borehole.

32. The apparatus of claim 31, further comprising at least one magnetically permeable member disposed between the two neighboring magnets.

* * * * *